(12) United States Patent
Miller et al.

(10) Patent No.: US 10,292,643 B2
(45) Date of Patent: May 21, 2019

(54) REAL TIME BRAIN TRAUMA TREATMENT

(71) Applicants: Landon C. G. Miller, Tuscaloosa, AL (US); Scott Behrens, Noblesville, IN (US); Kevin Butterfield, Noblesville, IN (US)

(72) Inventors: Landon C. G. Miller, Tuscaloosa, AL (US); Scott Behrens, Noblesville, IN (US); Kevin Butterfield, Noblesville, IN (US)

(73) Assignee: ASTROCYTICAL, INC., Tuscaloosa, AL (US)

( * ) Notice: Subject to any disclaimer, the term of this patent is extended or adjusted under 35 U.S.C. 154(b) by 661 days.

(21) Appl. No.: 14/878,763

(22) Filed: Oct. 8, 2015

(65) Prior Publication Data
US 2016/0100794 A1 Apr. 14, 2016

Related U.S. Application Data

(60) Provisional application No. 62/061,529, filed on Oct. 8, 2014.

(51) Int. Cl.
*A61B 5/00* (2006.01)
*A61F 7/00* (2006.01)
*A61F 7/10* (2006.01)
*A61B 90/00* (2016.01)
*A61B 5/0476* (2006.01)

(52) U.S. Cl.
CPC .......... *A61B 5/4836* (2013.01); *A61B 5/0006* (2013.01); *A61B 5/0476* (2013.01); *A61B 5/6803* (2013.01); *A61B 5/7282* (2013.01); *A61F 7/10* (2013.01);

(Continued)

(58) Field of Classification Search
CPC ... A61B 5/4833; A61B 5/0006; A61B 5/0476; A61B 5/6803; A61B 5/7282; A42B 3/285; A61F 2007/0056; A61F 2007/03
See application file for complete search history.

(56) References Cited

U.S. PATENT DOCUMENTS

| | | | | |
|---|---|---|---|---|
| 6,178,560 B1 * | 1/2001 | Halstead | ................. | A42B 3/122 2/413 |
| 6,228,106 B1 * | 5/2001 | Simbruner | ............. | A41B 13/00 2/69 |

(Continued)

*Primary Examiner* — Kaitlyn E Smith
(74) *Attorney, Agent, or Firm* — Avery N. Goldstein; Blue Filament Law PLLC

(57) ABSTRACT

Systems and methods are provided for rapidly introducing treatment to patients suffering traumatic brain injuries. A wearable map of the brain electroencephalography (EEG) points is worn in a headscarf, helmet, or other headgear for providing real-time information on a wearer's brain condition. The overall system includes an application (app) or program software that may run on a tablet, portable communication device, or computing device that processes the data from the EEG sensors and interprets the data in real time. If there is an accident or other stress forces experienced by the wearer that mimics a concussion, the system initiates the real-time ejection of a cooling agent within the headgear to provide a reduction in the victim's brain temperature with the helmet cooling system. A drug intervention system and injury detection app for expedited treatment of a potential brain injury during the critical early phases of the injury is also provided.

7 Claims, 5 Drawing Sheets

(52) U.S. Cl.
CPC . *A61B 2090/064* (2016.02); *A61F 2007/0002* (2013.01); *A61F 2007/0056* (2013.01)

(56) References Cited

U.S. PATENT DOCUMENTS

| | | | | |
|---|---|---|---|---|
| 6,277,143 B1* | 8/2001 | Klatz | A61F 7/00 | 607/104 |
| 7,296,304 B2* | 11/2007 | Goldsborough | A42B 3/285 | 2/171.3 |
| 7,827,620 B2* | 11/2010 | Feher | A42B 3/285 | 128/201.24 |
| 7,849,524 B1* | 12/2010 | Williamson | A42B 3/285 | 2/410 |
| 8,087,254 B2* | 1/2012 | Arnold | A41D 13/005 | 62/3.2 |
| 8,529,613 B2* | 9/2013 | Radziunas | A61F 7/10 | 607/110 |
| 9,669,185 B2* | 6/2017 | Nofzinger | A61M 21/02 | |
| 2002/0161349 A1* | 10/2002 | Allers | A61M 1/369 | 604/500 |
| 2005/0107855 A1* | 5/2005 | Lennox | A61F 7/10 | 607/104 |
| 2006/0030916 A1* | 2/2006 | Lennox | A61F 7/0085 | 607/104 |
| 2006/0074338 A1* | 4/2006 | Greenwald | A61B 5/0002 | 600/549 |
| 2006/0109630 A1* | 5/2006 | Colgan | H01L 23/42 | 361/718 |
| 2006/0189852 A1* | 8/2006 | Greenwald | A61B 5/0002 | 600/300 |
| 2007/0028370 A1* | 2/2007 | Seng | A41D 13/02 | 2/410 |
| 2008/0125288 A1* | 5/2008 | Case | A41D 1/002 | 482/1 |
| 2009/0023422 A1* | 1/2009 | MacInnis | A61B 5/0024 | 455/411 |
| 2009/0105605 A1* | 4/2009 | Abreu | A61B 5/0008 | 600/549 |
| 2010/0005572 A1* | 1/2010 | Chaplin | A42B 3/285 | 2/411 |
| 2010/0032132 A1* | 2/2010 | Collins | A42B 3/285 | 165/47 |
| 2010/0137951 A1* | 6/2010 | Lennox | A61F 7/02 | 607/104 |
| 2010/0319110 A1* | 12/2010 | Preston-Powers | A42B 3/285 | 2/422 |
| 2011/0125238 A1* | 5/2011 | Nofzinger | A61F 7/10 | 607/109 |
| 2011/0197613 A1* | 8/2011 | Pryor | F25D 3/14 | 62/259.3 |
| 2012/0150545 A1* | 6/2012 | Simon | A61B 5/0476 | 704/270 |
| 2012/0289869 A1* | 11/2012 | Tyler | A61N 7/00 | 601/2 |
| 2013/0019611 A1* | 1/2013 | Sims | F25B 21/02 | 62/3.3 |
| 2013/0053652 A1* | 2/2013 | Cooner | A61B 5/0476 | 600/301 |
| 2013/0090683 A1* | 4/2013 | Schock | A61F 7/0053 | 606/203 |
| 2013/0185837 A1* | 7/2013 | Phipps | A42B 3/12 | 2/2.5 |
| 2013/0211484 A1* | 8/2013 | Rozental | A42B 3/122 | 607/110 |
| 2013/0281797 A1* | 10/2013 | Sabesan | A61B 5/0205 | 600/301 |
| 2014/0031703 A1* | 1/2014 | Rayner | A61B 5/02055 | 600/484 |
| 2014/0163408 A1* | 6/2014 | Kocher | A61B 5/0476 | 600/544 |
| 2014/0196198 A1* | 7/2014 | Cohen | A42B 3/063 | 2/414 |
| 2014/0228649 A1* | 8/2014 | Rayner | A61B 5/1118 | 600/301 |
| 2014/0316230 A1* | 10/2014 | Denison | A61B 5/04012 | 600/383 |
| 2015/0040296 A1* | 2/2015 | Hanson | A42B 3/069 | 2/411 |
| 2015/0077246 A1* | 3/2015 | Eppler, Jr. | A42B 3/046 | 340/539.12 |
| 2015/0164172 A1* | 6/2015 | Linares | A42B 3/065 | 2/411 |
| 2015/0208750 A1* | 7/2015 | White | A61B 5/11 | 2/462 |
| 2015/0320588 A1* | 11/2015 | Connor | A61F 7/0097 | 607/107 |
| 2015/0351690 A1* | 12/2015 | Toth | A61B 5/6833 | 600/373 |
| 2016/0007910 A1* | 1/2016 | Boss | A61B 5/02055 | 600/301 |
| 2016/0143574 A1* | 5/2016 | Jones | A61B 5/4076 | 600/544 |
| 2016/0270656 A1* | 9/2016 | Samec | A61B 3/085 | |
| 2016/0270952 A1* | 9/2016 | Vergara | A61M 19/00 | |
| 2016/0331582 A1* | 11/2016 | Kozloski | A61F 7/10 | |
| 2016/0354232 A1* | 12/2016 | Rozental | A61F 7/10 | |
| 2016/0369861 A1* | 12/2016 | Phipps | B60R 19/28 | |
| 2017/0039045 A1* | 2/2017 | Abrahami | G06F 8/41 | |
| 2017/0100659 A1* | 4/2017 | Blecher | A63B 71/081 | |
| 2017/0135597 A1* | 5/2017 | Mann | A61B 5/0482 | |
| 2017/0209304 A1* | 7/2017 | Zumbrunnen | A61F 7/02 | |
| 2018/0064199 A1* | 3/2018 | Battis | A42B 3/286 | |
| 2018/0153246 A1* | 6/2018 | Baldi | A42B 3/04 | |

* cited by examiner

REAL TIME BRAIN TRAUMA TREATMENT

CROSS-REFERENCE TO RELATED APPLICATION

This application claims priority of U.S. Provisional Patent Application Ser. No. 62/061,529 filed Oct. 8, 2014, which is incorporated herein by reference.

FIELD OF THE INVENTION

The present invention in general relates to the field of medicine and in particular to a wearable platform for implementing real time brain trauma treatment.

BACKGROUND OF THE INVENTION

Traumatic brain injury (TBI), also known as intracranial injury, occurs when an external force traumatically injures the brain. TBI is a major cause of death and disability worldwide, especially in children and young adults. Males sustain traumatic brain injuries more frequently than do females. Causes of TBI include falls, vehicle accidents, sports injuries, and violence. Prevention measures include the use of technology to protect those suffering from automobile accidents, such as seat belts, and helmets for sporting participants or motorcycle users.

Brain trauma may occur as a consequence of a focal impact upon the head, by a sudden acceleration/deceleration within the cranium or by a complex combination of both movement and sudden impact. In addition to the damage caused at the moment of injury, brain trauma causes secondary injury, a variety of events that take place in the minutes and days following the injury. These processes, which include alterations in cerebral blood flow and the pressure within the skull, contribute substantially to the damage from the initial injury. Thus, the speed at which treatment is begun can have a substantial and positive impact for mitigating the long-term effects of TBI. FIG. 1 shows a general timeline in the form of brain trauma windows of amelioration opportunities for treatment of TBI.

The recognition of traumatic brain injuries especially in helmet wearing sports such as football and motor racing has increasingly been recognized in recent years, as well as the need to speedily treat these injuries. Thus there exist a need for improved devices and methods for rapidly introducing treatment to patients suffering traumatic brain injuries.

SUMMARY OF THE INVENTION

An automated method for rapidly introducing treatment to patients suffering traumatic brain injuries is provided that includes a wearable array of electroencephalography (EEG) sensors in electrical communication with a processor that controls a cooling mechanism and a communications capability; detecting whether there is an accident or other stress forces experienced by a wearer that mimics a concussion to the wearer's brain; and releasing a coolant in a series of tubes of the cooling mechanism to cool the wearer's brain in response to a detected accident or stress event.

An automated system for the rapid treatment of patients suffering traumatic brain injuries is provided that includes a wearable array of electroencephalography (EEG) sensors built into headwear, helmets, hoods, or headscarves, the EEG array in electrical communication with a processor that controls a cooling mechanism and a communications capability on a wearer's head; and a coolant in a series of tubes of the cooling mechanism to cool the wearer's brain in response to a detected accident or stress event.

BRIEF DESCRIPTION OF THE DRAWINGS

The present invention is further detailed with respect to the following drawings. These figures are not intended to limit the scope of the present invention but rather illustrate certain attributes thereof.

DESCRIPTION OF THE INVENTION

The present invention has utility as a method and system for rapidly introducing treatment to patients suffering traumatic brain injuries. Embodiments of the invention provide an integrated system of real time telemetry and active at-time-of-incident amelioration of potential and real forms of brain trauma. Embodiments of the invention are configured with a wearable map of the brain electroencephalography (EEG) points that may be worn in a headscarf, helmet, or other headgear for providing real-time information on a wearer's brain condition. EEG is the recording of electrical activity along the scalp. EEG measures voltage fluctuations resulting from ionic current flows within the neurons of the brain. In a specific embodiment the EEG sensors are wired to a racing car vehicle communication system that transmits the brain wave data in real time of the driver. In embodiments of the invention, the overall system includes an application (app) or program software that may run on a tablet, portable communication device, or computing device that processes the data from the EEG sensors and interprets the data in real time. In embodiments if there is an accident or other stress forces experienced by the wearer that mimics a concussion, the system initiates the real-time ejection of a cooling agent within the headgear to provide a net four degree reduction in the victim's brain temperature with the helmet cooling system, and alerts the car team of the situation. Embodiments of the invention may also include a drug intervention system kit and the injury detection app for expedited treatment of a potential brain injury during the critical early phases of the injury.

Figure 1:
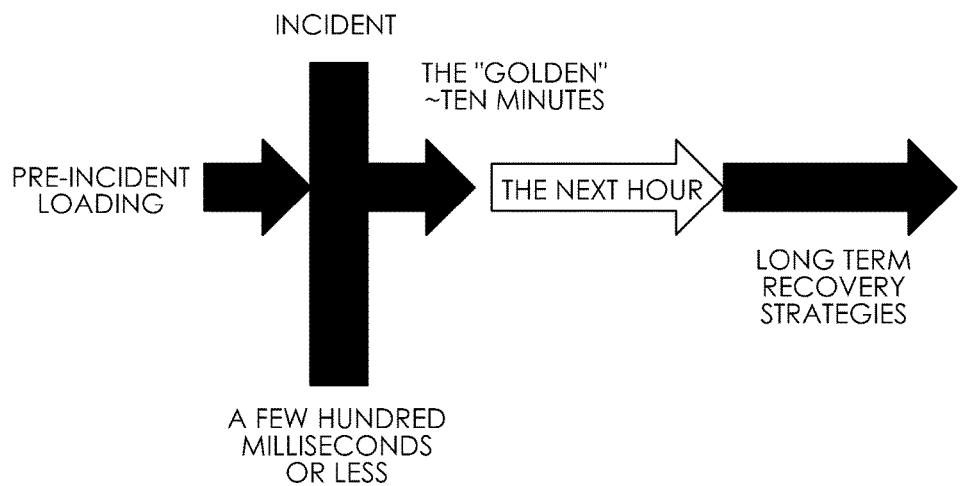
FIG. 1 is a block diagram showing the treatment stages for a traumatic brain injury.
Figure 2A:
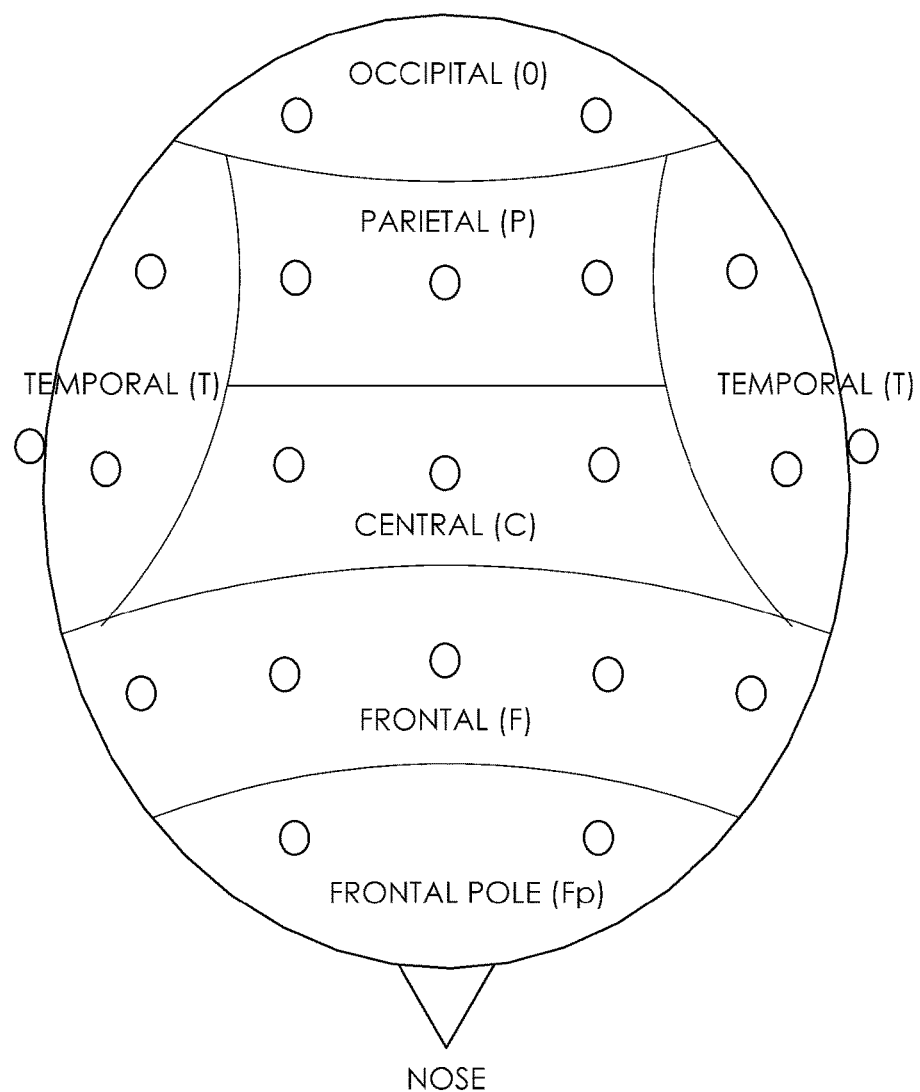
FIG. 2A is a placement map of electroencephalography (EEG)/quantitative electroencephalography (QEEG) sensor system overlaid on the regions of the human brain.
Figure 2B:
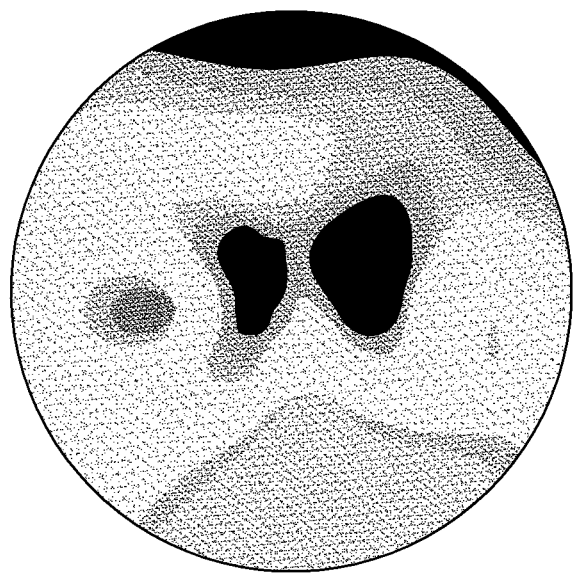
FIG. 2B is a color map of brainwave activity under concussion and normal brain state.
Figure 2B:
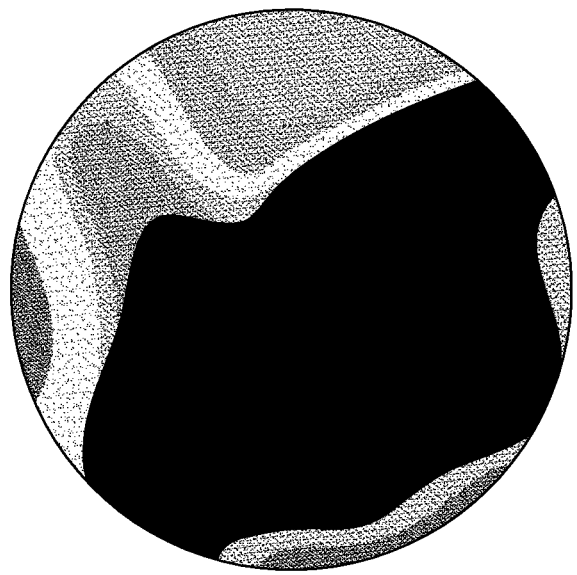
Figure 3A:
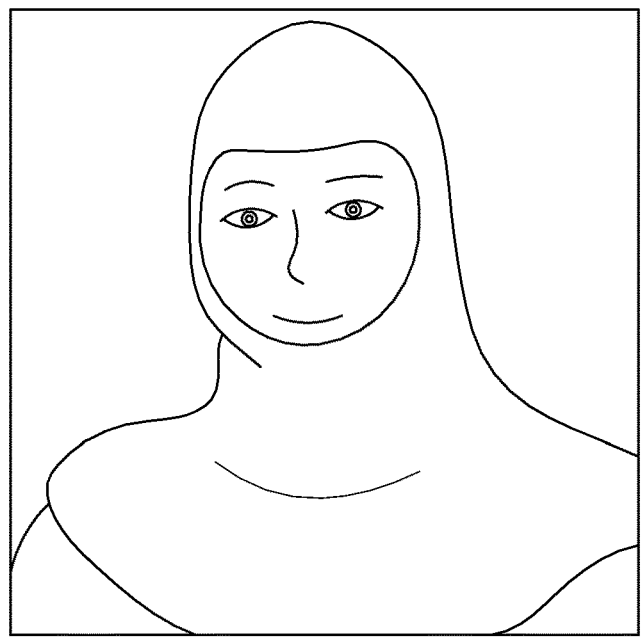
FIGS. 3A and 3B are photographs of an EEG/QEEG sensor system built into hood materials for implementing embodiments of the invention.
Figure 3B:
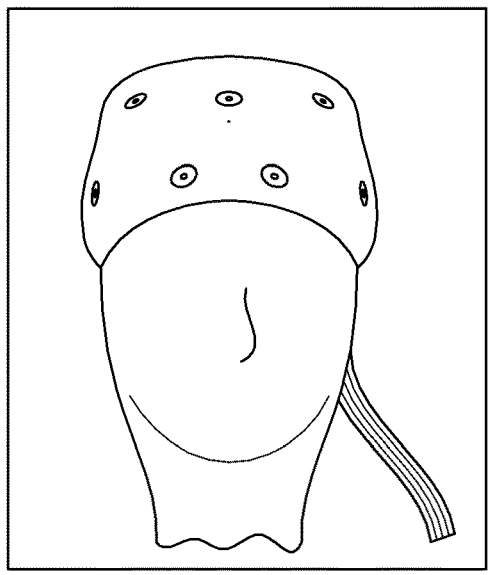

Referring now to the figures, FIG. 2A is a placement map of electroencephalography (EEG)/quantitative electroencephalography (QEEG) sensor array system overlaid on the regions of the human brain. FIG. 2B is a color map of brainwave activity under concussion and normal brain state as provided by the EEG sensor system. As shown in FIGS. 3A and 3B, the array of EEG sensors may be built into headwear, hoods, or headscarves that may be made of flame-resistant meta-aramid materials such as Nomex™ or other such materials. In addition the EEG sensors may be built into helmet strapping, helmet cushions, or both, depending upon the application. Illustrative examples of helmets include football, baseball, skiing, bicycle, police, security forces, construction, and other application that require wearer head protection.

Figure 4:
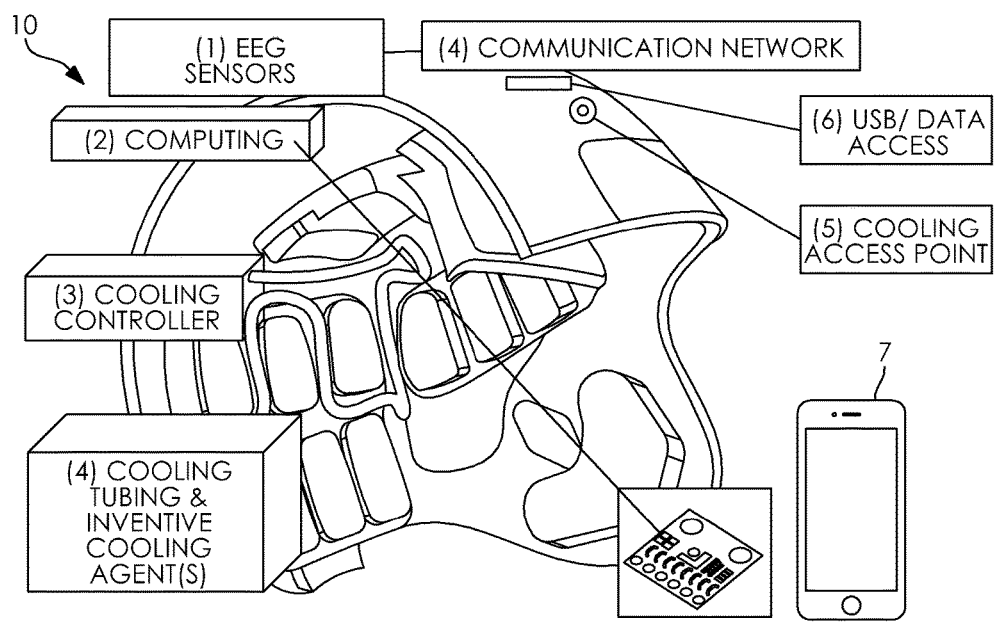
FIG. 4 is a partial perspective of a helmet with EEG/QEEG sensor system and a real-time process controlled cooling system with communication capabilities for introducing treatments to a wearer suffering a brain trauma injury according to an embodiment of the invention.

FIG. 4 is a partial perspective of a helmet 10 with EEG/QEEG sensor system (1) and a real-time process controlled cooling system (3, 4) with communication capabilities (4) for introducing treatments to a wearer suffering a brain trauma injury. Embodiments of the helmet 10 have the EEG sensors (1) built into the helmet strapping, helmet cushions, or both, depending upon the application, with a computing processor (2) and associated electronics including a set of, depending upon the application, accelerometers, strain gauges, gyroscopes, force sensors, and other such sensors to determine, in real time, the actions that are occurring as an incident to a wearer occurs. The computing processor controls a real-time process control cooling system that includes tubing holding unmixed or mixed coolant(s) (e.g., inventive entropic lipids, etc.) such that upon release of the coolants into the cooling tubing, the temperature of the center of the brain may have its temperature lowered from 2 to 4 degrees Fahrenheit. The temperature of the brain may be lowered in a time frame that ranges from some number of seconds to a couple of minutes, depending upon severity of the impact to the helmet, and other factors, with the lowered temperature maintained for at least an hour. The cooling system formed with the cooling tubing may be integrated into the padding or mesh in the headwear or helmet. In a specific embodiment an external supply of coolant may be attached to the headwear via a cooling access point (5). Embodiments of the helmet may also have a built in communication system for two-way data transmission of sufficient speed and bandwidth for data collection, analysis, and directive actions to take place in real-time. Communication may take place utilizing a wired universal serial bus (USB) or other wired connection port (6), or via wireless data transfer via Wi-fi/bluetooth/cellular/ digital radio, etc. Computing systems (7) and devices illustratively including a smart phone, tablet, desktop computer, laptop, or portable computing device, may inter-connect to the cooling and the EEG sensor systems.

In embodiments the EEG data collected may be analyzed and observations and recommendations may be made in real time including: type of injury predicted based on impact force; hookup of peripheral damage detection system; patient movement precautions; and interventional neuro-protective drug strategies to be introduced based on the EEG readings and locations of the brain injury. A graphical user interface (GUI) may be used to present the observations and recommendations.

The foregoing description is illustrative of particular embodiments of the invention, but is not meant to be a limitation upon the practice thereof. The following claims, including all equivalents thereof, are intended to define the scope of the invention.

The invention claimed is:

1. An automated method for rapidly introducing treatment to patients suffering traumatic brain injuries, said method comprising:
   providing in advance of injury, a helmet containing a wearable array of one or more electroencephalography (EEG) sensors and a real-time process controlled cooling system, in electrical communication with a processor that controls a cooling mechanism and a communications capability;
   detecting whether there is an accident or other stress forces experienced by a wearer that mimics a concussion to the wearer's brain with stress forces in real time with at least one of accelerometers, strain gauges, gyroscopes, or force sensors interpreted by software that both determines an event occurance and at least one of said wearable array of EEG sensor or said at least one of accelerometers, strain gauges, gyroscopes, or force sensors initiating process controlled cooling; and
   releasing a coolant in a series of tubes of the cooling mechanism to cool the wearer's brain in response to a detected accident or stress event.

2. The method of claim 1 wherein the wearer's brain is cooled from 2 to 4 degrees Fahrenheit.

3. The method of claim 1 wherein the temperature of the brain is lowered in a time frame that ranges in some seconds to a couple of minutes, depending upon severity of the accident or other stress forces experienced by the wearer.

4. The method of claim 1 wherein said wearable array is built into the helmet.

5. The method of claim 1 wherein said communications capability provides two-way data transmission utilizing at least one of Wi-fi, Bluetooth, cellular, or digital radio.

6. The method of claim 1 further comprising analyzing a set of data collected from said wearable array of one or more electroencephalography (EEG) sensors and making observations and recommendations including: type of injury predicted based on EEG and/or stress force analyses, hookup of a peripheral damage detection system, patient movement precautions, and interventional neuro-protective drug strategies to be introduced based on the EEG readings and locations of a brain injury.

7. The method of claim 1 further comprising alerting others that said coolant has been released.

\* \* \* \* \*